United States Patent
Gan et al.

(10) Patent No.: US 7,605,300 B2
(45) Date of Patent: Oct. 20, 2009

(54) GENETIC INSULATOR FOR PREVENTING INFLUENCE BY ANOTHER GENE PROMOTER

(75) Inventors: Susheng Gan, Lexington, KY (US); Mingtang Xie, Burnaby (CA)

(73) Assignee: University of Kentucky Research Foundation, Lexington, KY (US)

( * ) Notice: Subject to any disclaimer, the term of this patent is extended or adjusted under 35 U.S.C. 154(b) by 218 days.

(21) Appl. No.: 11/328,226

(22) Filed: Jan. 10, 2006

(65) Prior Publication Data

US 2006/0174370 A1    Aug. 3, 2006

Related U.S. Application Data

(62) Division of application No. 09/973,945, filed on Oct. 11, 2001, now abandoned.

(60) Provisional application No. 60/241,735, filed on Oct. 20, 2000.

(51) Int. Cl.
*C12N 15/82* (2006.01)

(52) U.S. Cl. .................................. 800/278

(58) Field of Classification Search ............... None
See application file for complete search history.

(56) References Cited

U.S. PATENT DOCUMENTS

| | | | |
|---|---|---|---|
| 5,610,053 | A | 3/1997 | Chung et al. |
| 6,037,525 | A | 3/2000 | Thompson et al. |
| 6,040,185 | A | 3/2000 | Dietrich et al. |
| 6,100,448 | A | 8/2000 | Thompson et al. |
| 6,229,070 | B1 | 5/2001 | Shinmyo et al. |
| 6,388,170 | B1 * | 5/2002 | Gan et al. .......... 800/278 |

FOREIGN PATENT DOCUMENTS

WO    WO 93/02187    2/1993

OTHER PUBLICATIONS

Millar et al. (1999, The Plant Cell 11:825-838).*

Gan, S. Ph.D. Thesis; Molecular characterization and genetic manipulation of plant senescence (University of Wisconsin-Madison, Madison, 1995).*
Millar et al., The Plant Cell, vol. 11, pp. 825-838, May 1999.
NCBI, GenBank, AF129511, 2000.
An G, "Binary Ti vectors for plant transformation and promoter analysis." In *Methods in Enzymology: Recombinant DNA*, R. Wu, and L. Grossman, eds., 292-305 (San Diego, Academic Press, 1987).
Bechtold N et al., "*In Planta Agrobacterium*-mediated gene transfer by infiltration of adult *Arabidopsis* plants", *C R Acad Sci Paris 316*, 1194-1199 (1993).
Brown M et al., "*lac* repressor can regulate expression from a hybrid SV40 early promoter containing a *lac* operator in animal cells", *Cell 49*, 603-612 (1987).
Gallie DR et al., "The 5'-leader sequence of tobacco mosaic virus RNA enhances the expression of foreign gene transcripts in vitro and in vivo". *Nucleic Acids Res 15*, 3257-3273 (1987).
Gan S. Ph.D. Thesis; *Molecular characterization and genetic manipulation of plant senescence* (University of Wisconsin-Madison, Madison, 1995).
Hajdukiewicz P et al., "The small, versatile *pPZP* family of *Agrobacterium* binary vectors for plant transformation", *Plant Mol Biol 25*, 989-994 (1994).
Holtorf S et al., "Comparison of different constitutive and inducible promoters for the overexpression of transgenes in *Arabidopsis thaliana*", *Plant Mol Biol 29*, 637-646 (1995).
Jefferson RA, "Assaying chimeric genes in plants: the GUS gene fusion system", *Plant Mol Biol Rep 5*, 387-405 (1987).
Sambrook J et al., *Molecular Cloning: A Laboratory Manual, Second edition* (New York, Cold Spring Harbor Laboratory Press, 1989).
Slomiany BA, "Extraction of nuclear proteins with increased DNA binding activity", *BioTechniques 28*, 938-942 (2000).
Mlynarova et al. Reduced Position Effect in Mature Transgenic Plants Conferred by the Chicken Lysozyme Matrix-Associated Region. The Plant Cell. Mar. 1994. vol. 6, pp. 417-426, see entire document.

* cited by examiner

*Primary Examiner*—David H Kruse
(74) *Attorney, Agent, or Firm*—McDermott Will & Emery LLP

(57) ABSTRACT

A 16 bp polynucleotide sequence of *Arabidopsis thaliana* is a genetic insulator that can effectively isolate a transgene from positional effects of neighboring gene activities in transgenic plant cells.

4 Claims, 4 Drawing Sheets

SEQUENCE LISTING

<160> NUMBER OF SEQ ID NOS: 38

<210> SEQ ID NO 1
<211> LENGTH: 58
<212> TYPE: DNA
<213> ORGANISM: Arabidopsis thaliana

<400> SEQUENCE: 1
gaagatctag aatatatata tattcgatag aatatatata tattcgcaag acccttcc          58

<210> SEQ ID NO 2
<211> LENGTH: 35
<212> TYPE: DNA
<213> ORGANISM: Arabidopsis thaliana

<400> SEQUENCE: 2
ggaattccat ggatcccggg tgtaattgta aatag                                   35

<210> SEQ ID NO 3
<211> LENGTH: 30
<212> TYPE: DNA
<213> ORGANISM: Arabidopsis thaliana

<400> SEQUENCE: 3
gaagatctga tatcaagctt cgcaagaccc                                         30

<210> SEQ ID NO 4
<211> LENGTH: 63
<212> TYPE: DNA
<213> ORGANISM: Arabidopsis thaliana

<400> SEQUENCE: 4
gaagatctat tgtgagcgct cacaatgata attgtgagcg ctcacaattc gcaagaccct        60
tcc                                                                      63

<210> SEQ ID NO 5
<211> LENGTH: 46
<212> TYPE: DNA
<213> ORGANISM: Arabidopsis thaliana

<400> SEQUENCE: 5
gaagatctag aatatatata tattcactag ttcgcaagac ccttcc                       46

<210> SEQ ID NO 6
<211> LENGTH: 18
<212> TYPE: DNA
<213> ORGANISM: Escherichia coli

<400> SEQUENCE: 6
attgtgagcg ctcacaat                                                      18

<210> SEQ ID NO 7
<211> LENGTH: 31
<212> TYPE: DNA
<213> ORGANISM: Escherichia coli

<400> SEQUENCE: 7
cttctaattg tgagcgctca caatgaaaaa g                                       31

<210> SEQ ID NO 8
<211> LENGTH: 31

```
<212> TYPE: DNA
<213> ORGANISM: Escherichia coli

<400> SEQUENCE: 8 cttttcatt gtgagcgctc acaattagaa g                              31

<210> SEQ ID NO 9
<211> LENGTH: 16
<212> TYPE: DNA
<213> ORGANISM: Arabidopsis thaliana

<400> SEQUENCE: 9
gaatatatat atattc                                              16

<210> SEQ ID NO 10
<211> LENGTH: 16
<212> TYPE: DNA
<213> ORGANISM: Arabidopsis thaliana

<400> SEQUENCE: 10
gaatatatat atattc                                              16

<210> SEQ ID NO 11
<211> LENGTH: 29
<212> TYPE: DNA
<213> ORGANISM: Arabidopsis thaliana

<400> SEQUENCE: 11
cttctagaat atatatatat tcgaaaaag                                29

<210> SEQ ID NO 12
<211> LENGTH: 29
<212> TYPE: DNA
<213> ORGANISM: Arabidopsis thaliana

<400> SEQUENCE: 12 cttttcgaa tatatatata ttctagaag                                 29

<210> SEQ ID NO 13
<211> LENGTH: 29
<212> TYPE: DNA
<213> ORGANISM: Arabidopsis thaliana

<400> SEQUENCE: 13
cttctagaat atgtatat tcgaaaaag                                  29

<210> SEQ ID NO 14
<211> LENGTH: 29
<212> TYPE: DNA
<213> ORGANISM: Arabidopsis thaliana

<400> SEQUENCE: 14 cttttcgaa tatacatata ttctagaag                                 29

<210> SEQ ID NO 15
<211> LENGTH: 29
<212> TYPE: DNA
<213> ORGANISM: Arabidopsis thaliana

<400> SEQUENCE: 15
cttctaacct atatatat tcgaaaaag                                  29

<210> SEQ ID NO 16
```

```
<211> LENGTH: 29
<212> TYPE: DNA
<213> ORGANISM: Arabidopsis thaliana

<400> SEQUENCE: 16 cttttcgaa tatatatata ggttagaag                              29

<210> SEQ ID NO 17
<211> LENGTH: 29
<212> TYPE: DNA
<213> ORGANISM: Arabidopsis thaliana

<400> SEQUENCE: 17
cttctagaag cgatatatat tcgaaaaag                             29

<210> SEQ ID NO 18
<211> LENGTH: 29
<212> TYPE: DNA
<213> ORGANISM: Arabidopsis thaliana

<400> SEQUENCE: 18 cttttcgaa tatatatcgc ttctagaag                              29

<210> SEQ ID NO 19
<211> LENGTH: 29
<212> TYPE: DNA
<213> ORGANISM: Arabidopsis thaliana

<400> SEQUENCE: 19
cttctagaat atcgcgatat tcgaaaaag                             29

<210> SEQ ID NO 20
<211> LENGTH: 29
<212> TYPE: DNA
<213> ORGANISM: Arabidopsis thaliana

<400> SEQUENCE: 20 cttttcgaa tatcgcgata ttctagaag                              29

<210> SEQ ID NO 21
<211> LENGTH: 29
<212> TYPE: DNA
<213> ORGANISM: Arabidopsis thaliana

<400> SEQUENCE: 21
cttctagaat atctatatat tcgaaaaag                             29

<210> SEQ ID NO 22
<211> LENGTH: 29
<212> TYPE: DNA
<213> ORGANISM: Arabidopsis thaliana

<400> SEQUENCE: 22 cttttcgaa tatatagata ttctagaag                              29

<210> SEQ ID NO 23
<211> LENGTH: 29
<212> TYPE: DNA
<213> ORGANISM: Arabidopsis thaliana

<400> SEQUENCE: 23
cttctagaat atagatatat tcgaaaaag                             29
```

<210> SEQ ID NO 24
<211> LENGTH: 29
<212> TYPE: DNA
<213> ORGANISM: Arabidopsis thaliana

<400> SEQUENCE: 24 cttttcgaa tatatctata ttctagaag         29

<210> SEQ ID NO 25
<211> LENGTH: 29
<212> TYPE: DNA
<213> ORGANISM: Arabidopsis thaliana

<400> SEQUENCE: 25
cttctagaat atatctatat tcgaaaaag         29

<210> SEQ ID NO 26
<211> LENGTH: 29
<212> TYPE: DNA
<213> ORGANISM: Arabidopsis thaliana

<400> SEQUENCE: 26 cttttcgaa tatagatata ttctagaag         29

<210> SEQ ID NO 27
<211> LENGTH: 29
<212> TYPE: DNA
<213> ORGANISM: Arabidopsis thaliana

<400> SEQUENCE: 27
cttctagaat atatagatat tcgaaaaag         29

<210> SEQ ID NO 28
<211> LENGTH: 31
<212> TYPE: DNA
<213> ORGANISM: Arabidopsis thaliana

<400> SEQUENCE: 28 cttttcgaa tatctatata tattctagaa g         31

<210> SEQ ID NO 29
<211> LENGTH: 16
<212> TYPE: DNA
<213> ORGANISM: Arabidopsis thaliana

<400> SEQUENCE: 29
gaatatatgt atattc         16

<210> SEQ ID NO 30
<211> LENGTH: 16
<212> TYPE: DNA
<213> ORGANISM: Arabidopsis thaliana

<400> SEQUENCE: 30
acctatatat atattc         16

<210> SEQ ID NO 31
<211> LENGTH: 16
<212> TYPE: DNA
<213> ORGANISM: Arabidopsis thaliana

<400> SEQUENCE: 31
gaagcgatat atattc         16

<210> SEQ ID NO 32
<211> LENGTH: 16
<212> TYPE: DNA
<213> ORGANISM: Arabidopsis thaliana

<400> SEQUENCE: 32
gaatatcgcg atattc                                                    16

<210> SEQ ID NO 33
<211> LENGTH: 16
<212> TYPE: DNA
<213> ORGANISM: Arabidopsis thaliana

<400> SEQUENCE: 33
gaatatctat atattc                                                    16

<210> SEQ ID NO 34
<211> LENGTH: 16
<212> TYPE: DNA
<213> ORGANISM: Arabidopsis thaliana

<400> SEQUENCE: 34
gaatatagat atattc                                                    16

<210> SEQ ID NO 35
<211> LENGTH: 16
<212> TYPE: DNA
<213> ORGANISM: Arabidopsis thaliana

<400> SEQUENCE: 35
gaatatatct atattc                                                    16

<210> SEQ ID NO 36
<211> LENGTH: 16
<212> TYPE: DNA
<213> ORGANISM: Arabidopsis thaliana

<400> SEQUENCE: 36
gaatatatag atattc                                                    16

<210> SEQ ID NO 37
<211> LENGTH: 16
<212> TYPE: DNA
<213> ORGANISM: Arabidopsis thaliana
<220> FEATURE:
<221> NAME/KEY: misc_feature
<222> LOCATION: (1)..(6)
<223> OTHER INFORMATION: N can be any nucleotide
<220> FEATURE:
<221> NAME/KEY: misc_feature
<222> LOCATION: (7)..(10)
<223> OTHER INFORMATION: NNNN is not CGCG
<220> FEATURE:
<221> NAME/KEY: misc_feature
<222> LOCATION: (7)..(8)
<223> OTHER INFORMATION: N is not G
<220> FEATURE:
<221> NAME/KEY: misc_feature
<222> LOCATION: (9)..(9)
<223> OTHER INFORMATION: N can be any nucleotide
<220> FEATURE:
<221> NAME/KEY: misc_feature
<222> LOCATION: (10)..(10)
<223> OTHER INFORMATION: N is not G

<400> SEQUENCE: 37
nnnnnnnnnn atattc                                                    16

```
<210> SEQ ID NO 38
<211> LENGTH: 18
<212> TYPE: DNA
<213> ORGANISM: Escherichia coli

<400> SEQUENCE: 38
taacactcgc gagtgtta                                                 18
```

GENETIC INSULATOR FOR PREVENTING INFLUENCE BY ANOTHER GENE PROMOTER

RELATED APPLICATIONS

This application is a divisional of application Ser. No. 09/973,945, filed Oct. 11, 2001 now abadoned, which claims priority of U.S. Application No. 60/241,735, filed Oct. 20, 2000, the contents of which are hereby incorporated by reference.

FIELD OF THE INVENTION

The invention relates to the field of plant molecular biology and biotechnology. Specifically, the invention relates to polynucleotide sequences that can minimize or eliminate the position effect on a transgene in a plant.

BACKGROUND OF THE INVENTION

Transgenic technology is widely used in biotechnology. In eukaryotes, the temporal and spatial expression of transgenes is regulated by transcription factors through their interaction with enhancer elements. However, eukaryotic enhancer-promoter interactions lack the specificity for precise temporal and spatial patterns of transgenic expression. The expression of a transgene can be affected by (a) the promoter of a selectable marker gene that is closely linked with the transgene, and/or (b) by chromosomal genes that flank the transgene, which is often referred to as the "position effect". These effects are often not desirable, especially when tissue-specific, precisely controlled, or optimal transgene expression is wanted.

It is known that a eukaryotic genome has organizational properties that rely on the ability of the chromosome to establish autonomous functional units. The polynucleotide sequences that separate these domains are called genetic insulator elements. These genetic insulator elements can buffer a transgene from position effects, so that an introduced transgene can be expressed independent of its location in the chromosome. In addition, a genetic insulator may repress nonspecific interactions between enhancers and promoters. Thus, it could be possible to obtain precise gene expression by using an appropriate genetic insulator to shield the effects of neighboring gene promoters.

Genetic insulators in fruit fly (*Drosophila*) include specialized chromatin structures (scs and scs'), which consist of 350 base pairs (bp) and 200 bp, respectively. These sequences are associated with chromatin structures and serve as boundaries that can prevent activation by enhancer elements. Similarly, genetic insulators are known in the chicken in the form of lysozyme "A" element and the β-globin LCR (HS4), which contain 242 bp. These insulators generally comprise 200-250 bp and function directionally. Additionally, the gypsy chromatin insulator of *Drosophila* (originally isolated from the gypsy retrotransposon) protects a gene and its regulatory elements from both positive and negative position effects (see, U.S. Pat. No. 6,229,070, incorporated by reference).

By contrast, there previously have been no genetic insulators isolated from plants. There is a need in the art to develop a plant genetic insulator to control transgene expression in plants.

SUMMARY OF THE INVENTION

The invention provides an isolated polynucleotide that contains at least one copy of either a polynucleotide region having the sequence set forth in SEQ ID NO:9 (5'GAATATATATATATTC3') or a polynucleotide region having a sequence that is a variant or fragment of the sequence set forth in SEQ ID NO:9, wherein the polynucleotide region has a genetic insulator activity. In various embodiments, the polynucleotide has a sequence as set forth in SEQ ID NOS:1, 5, 9, 10, 11, 12, 15, 16, 17, 18, 21, 22, 23, 24, 25, 26, 27, 28, 30, 31, 33, 34, 35 or 36. In one embodiment, the plant genetic insulator sequence contains only 16 base pair (bp), and is completely distinct in size and function from the genetic insulators of fruit fly and chicken.

The invention provides a recombinant polynucleotide containing a plant genetic insulator comprising at least one copy of a polynucleotide having the sequence set forth in SEQ ID NO:9 (5'GAATATATATATATTC3') or a polynucleotide region having a sequence that is a variant or fragment of the sequence set forth in SEQ ID NO:9, wherein the polynucleotide region has a genetic insulator activity.

The invention also provides a vector, comprising: a replicable vector; and the nucleic acid mentioned above that is inserted into the vector. Preferably, the vector is an expression vector, a plant vector, or a plant expression vector. The invention also provides a host cell, in which the vector is situated. The host cell may be a plant cell or a microorganism.

The invention further provides a transgenic plant containing the genetic insulator polynucleotide. The invention is also directed to a recombinant seed containing the genetic insulator polynucleotide.

The invention provides a method for expressing a polypeptide in an organism comprising: constructing a vector comprising the genetic insulator polynucleotide; inserting the vector into the organism, wherein the genetic insulator sequence is recombined into the organism; and allowing the organism to express the polypeptide. In this method, the polypeptide may be encoded on an insert in the vector. Alternatively, the polypeptide may be encoded on the genome of organism. Further, the described nucleic acid may be inserted immediately upstream of the nucleic acid encoding the polypeptide. Preferably, the organism is a plant. More preferably, the plant may be *Arabidopsis* or tobacco.

BRIEF DESCRIPTION OF THE DRAWINGS

FIG. 3A is an autoradiograph of EMSA. 5 µg (Lane 2) or 9 µg (Lanes 3-7) of *Arabidopsis* nuclear proteins (NPs) were co-incubated with $^{32}$P-labeled insulator (NI29) or lacO (L31), respectively. There was 0—(Lane 3), 2—(Lane 4), 20—(Lane 5), or 200-fold (Lane 6) molar excess of cold N129 competitor. FIG. 3B is a bar graph showing the relative amount of CX formed in each lane. The amount of CX in Lane 3 was set as 100 FP are the free probes. + or − indicate with or without NPs added, respectively.

FIG. 4A is a set of the sequences of DNA probes. Only one strand is shown. The capital letters are the perfect palindromic sequence or its derivatives/mutants. The small letters represent the native sequences flanking the palindrome in *Arabidopsis*. N129, the native insulator. NIm, naturally occurring mutant of N129. M1-M7 are artificial mutants/derivatives of NI29. FIG. 4B and FIG. 4C are autoradiographs of EMSA. FIG. 4D and FIG. 4E are bar graphs showing the quantitative analysis of CX shown in FIG. 4B and FIG. 4C, respectively. The amount of CX formed in each lane was normalized to the amount of CX formed in Lane 2 of respective autoradiographs. Note the scale difference of the Y-axes between FIG. 4D and FIG. 4E. CX is the insulator-nuclear protein complex. FP are the free probes. NPs are the *Arabidopsis* nuclear proteins. + or − indicate with or without NPs added, respectively.

DETAILED DESCRIPTION OF THE INVENTION

Figure 1:
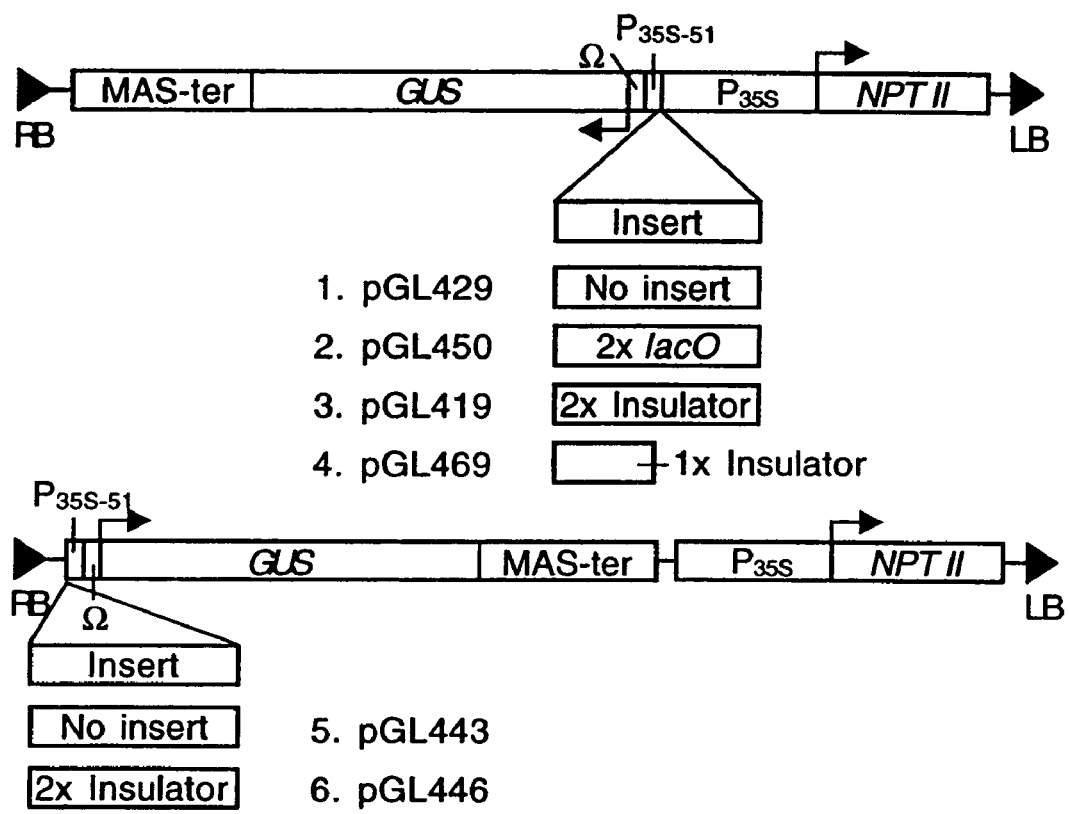
FIG. 1 is a schematic drawing showing constructs used to investigate the buffering role of the insulator. 1× or 2× represents 1 copy or 2 copies, respectively. lacO, the mutated 18-bp lac Operator sequence that possesses a perfect palindromic structure. GUS, the reporter gene encoding β-glucuronidase. NPT II, a gene encoding neomycin phosphotransferase II that renders transgenic plant cells resistant to kanamycin. Ω is the TMV Ω leader sequence. $P_{35S}$ is the cauliflower mosaic virus (CaMV) 35S promoter. $P_{35Smini-35}$ is the minimum promoter (−35 region) of the CaMV 35S promoter. RB and LB are the right and left border of T-DNA, respectively.

The invention is directed to a polynucleotide cloned from *Arabidopsis thaliana*, and variants thereof, that possesses genetic insulating activity. In one embodiment, the specifically exemplified insulator sequence is a polynucleotide having a 16 bp sequence that displays a perfect palindrome structure (5'GAATATATATATATTC3'; SEQ ID NO:9).

As used herein, the terms "insulator", "genetic insulator" and "insulator sequence" refer to a nucleic acid sequence that, when it is inserted upstream of a gene of interest, prevents the influence of other nearby regulatory sequences in the expression of the gene of interest. The term "insulator" (or "genetic insulator"; "chromatin insulator", or "boundary element") thus has its conventional meaning in the art, and refers to a DNA segment that prevents enhances located on one side of the insulator or boundary element from acting on promoters located in the adjacent domain (see, U.S. Pat. No. 6,037,525, incorporated by reference).

Preferably, the genetic insulator is a plant insulator. The term "plant insulator" means that the insulator is functional in a plant, and includes insulators isolated from plants. Plant genetic insulators of the invention may be taken from any suitable plant, including those plants specified below; but insulator with appropriate sequences may be taken from any suitable animal including insects (e.g., *Drosophila*), mammals (e.g., rat, mouse, dog, cat), birds (e.g., chicken, turkey), etc.; and insulators may be taken from other eukaryotes such as fungi (e.g., *Saccharomyces cereviceae*). Where two insulators are employed, they may be the same or different sequences. The insulator may be a variant of a naturally occurring insulator, so long as it retains function as an insulator.

Sequence Identity. The exemplified insulator sequence (5'GAATATATATATATTC3'; SEQ ID NO:9) has been isolated from *Arabidopsis*. However, other variations and analogs that have the desired effect of allowing the transgene of interest to be expressed from its specified control elements without the influence of neighboring regulatory elements are also within the purview of the invention (for some of the acceptable variants, see TABLE 3, below). This disclosure sets forth several examples of experiments in which the insulator sequences are mutated and their ability to insulate the gene of interest is assayed. Thus, the insulator may be any variant or fragment of the exemplified sequence that has insulator activity. Also, the insulator may be any variant or fragment of the exemplified sequence that hybridizes to the polynucleotide exemplified sequence under 5×SSC and 42° C. wash conditions (see, Sambrook et al., *Molecular Cloning: A Laboratory Manual*, 2d Ed. (Cold Spring Harbor Laboratory, Cold Spring Harbor, New York, 1989)).

Two polynucleotide sequences are said to be "identical" if the sequence of residues is the same when aligned for maximum correspondence as described below. The term "complementary" applies to nucleic acid sequences and is used herein to mean that the sequence is complementary to all or a portion of a reference polynucleotide sequence.

Optimal alignment of sequences for comparison can be conducted by the local homology algorithm of Smith & Waterman, *Add. Appl. Math.*, 2:482 (1981), by the homology alignment method of Needleman & Wunsch, *J. Mol. Biol.*, 48:443 (1970), by the search for similarity method of Pearson & Lippman, *Proc. Natl. Acad. Sci. USA*, 85:2444 (1988), or the like. Computer implementations of the above algorithms are known as part of the Genetics Computer Group (GCG) Wisconsin Genetics Software Package (GAP, BESTFIT, BLASTA, FASTA and TFASTA), 575 Science Drive, Madison, Wis.

"Percentage of sequence identity" is determined by comparing two optimally aligned sequences over a comparison window, wherein the portion of the sequence in the comparison window may comprise additions or deletions (i.e. "gaps") as compared to the reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence.

Use of the Genetic Insulator of the Invention. One of the main problems of current transgenic techniques is the gradual loss of expression of the transfected gene, perhaps due to the repressive influence of the DNA sequences that surround the integration site of the transfected gene. By insulating a gene to be transfected with the genetic insulator of the invention, the gene could be usefully maintained in an active state.

The insulator sequence can be placed upstream or downstream of the gene of interest to have the insulating effect on the gene. For example, the insulator sequence may be positioned upstream of the gene of interest. At least one copy of the insulator sequence may be used in the invention.

While the invention can be used to specifically to tightly control the expression of transgenes, it is also possible to use the insulator sequence to more tightly control endogenous genes by inserting the insulator sequence upstream of the endogenous gene of interest.

Advantageously, the function of the insulator element is independent of its orientation, and thus the insulator can function when placed in genomic or reverse genomic orientation with respect to the transcription unit. Also, only one copy of the insular need be introduced into the plant to achieve effective insulator function (contrast, U.S. Pat. No. 6,037,525, incorporated by reference.)

The genetic insulator of the invention can also be a useful tool in gene regulation studies and in the production of stably transfected cell lines. Because the expression of a stably transfected gene is influenced by adjacent regulatory elements near the site of gene integration, insulating the transfected gene with the genetic insulator of the invention eliminates the variability that is caused by cell-to-cell differences in integration position and in the random sites of integration. This should obviate the need for numerous founder lines of clonal cell lines.

Polynucleotide Constructs. A variety of enhancers, promoters, and genes are suitable for use in the constructs of the invention, and that the constructs will contain the necessary start, termination, and control sequences for proper transcription and processing of the gene of interest when the construct is introduced into a mammalian or a higher eukaryotic cell. DNA constructs known as "expression cassettes," preferably include a transcription initiation region, a structural gene (a structural polynucleotide coding for a polypeptide) positioned downstream from the transcription initiation region and operatively associated therewith, an insulator positioned: (i) 5' to the transcription initiation region, (ii) 3' to the structural gene, or (iii) both 5' to the transcription initiation region and 3' to the structural polynucleotide coding for a polypeptide, and, optionally, a termination sequence including stop signal for RNA polymerase and a polyadenylation signal for polyadenylase. The promoter should be capable of operating in the cells to be transformed. The termination region may be derived from the same gene as the promoter region, or may be derived from a different gene.

The term "operatively associated," as used herein, refers to polynucleotide regions on a single polynucleotide molecule that are associated, so that the fumction of one affects the function of the other. Thus, a transcription initiation region is operatively associated with a structural gene when it is capable of affecting the expression of that structural gene (i.e., the structural gene is under the transcriptional control of the transcription initiation region). In other words, the polynucleotide sequences described herein are "operably linked" with other polynucleotide sequences. DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous (or in close proximity to) and, in the case of secretory leaders, contiguous and in reading phase. The transcription initiation region is said to be "upstream" from the structural gene, which is in turn said to be "downstream" from the transcription initiation region.

The transcription initiation region, which includes the RNA polymerase binding site (promoter), may be native to the host plant to be transformed or may be derived from an alternative source, where the region is functional in the host plant. Other sources include the Agrobacterium T-DNA genes, such as the transcriptional initiation regions for the biosynthesis of nopaline, octapine, mannopine, or other opine transcriptional initiation regions; transcriptional initiation regions from plants, such as the ubiquitin promoter; root specific promoters; transcriptional initiation regions from viruses (including host specific viruses), or partially or wholly synthetic transcription initiation regions. Transcriptional initiation and termination regions are well known. The transcriptional initiation regions may, in addition to the RNA polymerase binding site, include regions that regulate transcription, where the regulation involves, for example, chemical or physical repression or induction. Thus, the transcriptional initiation region, or the regulatory portion of such region, is obtained from an appropriate gene that is so regulated.

The term "structural gene" refers to those portions of genes which comprise a DNA segment coding for a protein, polypeptide, or portion thereof, possibly including a ribosome binding site and/or a translational start codon, but lacking a transcription initiation region. The term can also refer to transgenic copies of a structural gene not naturally found within a cell but artificially introduced. The structural gene may encode a protein not normally found in the plant cell in which the gene is introduced or in combination with the transcription initiation region to which it is operationally associated, in which case it is termed a heterologous structural gene. Genes that may be operationally associated with a transcription initiation region of the present invention for expression in a plant species may be derived from a chromosomal gene, cDNA, a synthetic gene, or combinations thereof.

The term "transgene" refers to a gene that is artificially transferred into, and maintained, and may be expressed in host organisms such as plants. Various techniques are amply exemplified in the literature and find particular exemplification in Sambrook et al., *Molecular Cloning: A Laboratory Manual*, 2d Ed. (Cold Spring Harbor Laboratory, Cold Spring Harbor, N.Y., 1989) and other standard texts.

As used herein, a transgenic plant refers to a plant in which at least some cells are stably transformed with a heterologous DNA construct. As used herein, a heterologous DNA construct refers to DNA that is artificially introduced into a cell or into a cell's ancestor. Such DNA may contain genes or DNA which would not normally be found in the cell to be transformed, or may contain genes or DNA which is contained in the cell to be transformed. In the latter case, cells are transformed so that they contain additional or multiple copies of the DNA sequence or gene of interest. DNA constructs may be introduced into cells by a variety of gene transfer methods known to those skilled in the art, for example, gene transfection, microinjection, electroporation, and infection.

The polynucleotide constructs of the invention may be used in gene transfer methods to allow the protected expression of one or more given genes that are stably transfected into the cellular plant DNA ("recombinant" polynucleotides of the invention). Recombinant polynucleotide constructs comprising one or more of the genetic insulator polynucleotide sequences described herein and an additional polynucleotide sequence are included within the scope of this invention. These recombinant DNA constructs have sequences that (1) do not occur in nature; (2) exist in a form that does not occur in nature; or (3) exist in association with other materials that do not occur in nature. The constructs of the invention would not only insulate a transfected gene or genes from the influences of DNA surrounding the site of integration, but would also prevent the integrated constructs from impacting on the DNA at the site of integration and would therefore prevent activation of the transcription of genes that are harmful or detrimental to the cell.

Transcriptionally competent transcription units can be made by conventional techniques (see, Sambrook et al., *Molecular Cloning: A Laboratory Manual*, 2d Ed. (Cold Spring Harbor Laboratory, Cold Spring Harbor, N.Y., 1989)). The comparatively small size of the insulator of the invention (contrast, U.S. Pat. Nos. 5,610,053 and 6,037,525, each incorporated by reference) makes for easier use of the insulator sequences. In general, the insulator of the invention is placed in sufficient proximity to the enhancer so that it is functionally active to buffer the effects of a cis-acting DNA region on the promoter of the transcription unit. However, in some cases, the insulator can be placed distantly from the transcription unit. The optimal location of the insulator element can be determined by routine experimentation for any particular DNA construct, with additional guidance provided by the location of the genetic insulator in non-transgenic plant DNA, for example, in Arabidopsis DNA.

Vectors. The invention is further directed to a replicable vector containing the insulator sequence and cDNA which may code for a polypeptide and which is capable of expressing the polypeptide under the transcriptional control of a promoter. The vector is transferable to the host organism. Preferably, the host organism is a plant or plant cell. The vector may be an integrating or non-integrating vector and is conveniently a plasmid.

Vectors that may be used to transform plant tissue with DNA constructs of the invention include *Agrobacterium* vectors, non-*Agrobacterium* vectors, as well as other known plant vectors suitable for DNA-mediated transformation. In general, *Agrobacterium* vectors comprise an agrobacterium, typically *Agrobacterium tumefaciens*, that carry at least one tumor-inducing (or "Ti") plasmid. When the agrobacterium is *Agrobacterium rhizogenes*, this plasmid is also known as the root-inducing (or "Ri") plasmid. The Ti (or Ri) plasmid contains DNA referred to as "T-DNA" that is transferred to the cells of a host plant when that plant is infected by the agrobacterium. In an *Agrobacterium* vector, the T-DNA is modified by genetic engineering techniques to contain the "expression cassette", or the gene or genes of interest to be expressed in the transformed plant cells, along with the associated regulatory sequences. Such *Agrobacterium* vectors are useful for introducing foreign genes into a variety of plant species, and are particularly useful for the transformation of dicots.

Vector Containing a Particular Genetic Insulator Sequence. To investigate the function of the 16 bp sequence (SEQ ID NO:9), we first made a construct called pGL419 (construct 3 in FIG. 1) in which two copies of the 16 bp palindrome were fused with a 35S minimum promoter-GUS. As controls, we constructed pGL429 (construct 1 in FIG. 1; a bidirectional promoter construct shown in a separate disclosure) and pGL450 (which is essentially the same as pGL419 except that 2 copies of mutated 18 bp lac operator sequence were used instead of the 16 bp insulator sequence). Like the 16 bp insulator, the mutated lac operator is a perfect palindrome.

Transgenic *Arabidopsis* plants containing either pGL429 or pGL450 showed constitutive GUS expression. However, none of the transgenic plants harboring pGL419 showed any GUS expression, suggesting that the 16 bp insulator can insulate the GUS gene from the enhancers of the 35S promoter. Moreover, by constructing pGL469 (construct 4 in FIG. 1), we found that one copy of the 16 bp insulator is sufficient for the insulation activity.

Additional details of construction of vectors containing an insulator of the invention (including pGL419 and pGL469) is provided in EXAMPLE 1.

Methods for the Demonstration of Insulator Function. To test a candidate insulator for activity as an insulator, one may simply clone the candidate insulator into a construct comprising, 5' to 3', a constitutive enhancer, the candidate insulator, an inducible promoter (e.g., an HSP70 promoter), and a reporter gene (e.g., GUS or luciferase). Plant cells are then transformed with the construct by any suitable means as described herein, and (optionally) plants created from the cells. See, EXAMPLE 1, below.

More particularly, a position effect on a transgene is generally exerted by the promoters/enhancers of neighboring genes. This position effect can be demonstrated in either of the following two ways.

One way is to use a constitutive promoter fused to the reporter gene GUS. Transgenic plants containing this construct should display a spectrum of the GUS expression level, with some plants expressing GUS at a very high level and some other plants at lesser levels. The addition of the insulator sequence at the 5' end of the constitutive promoter should result in an even level of GUS expression with no or little variation among all transgenic plants.

Figure 2:
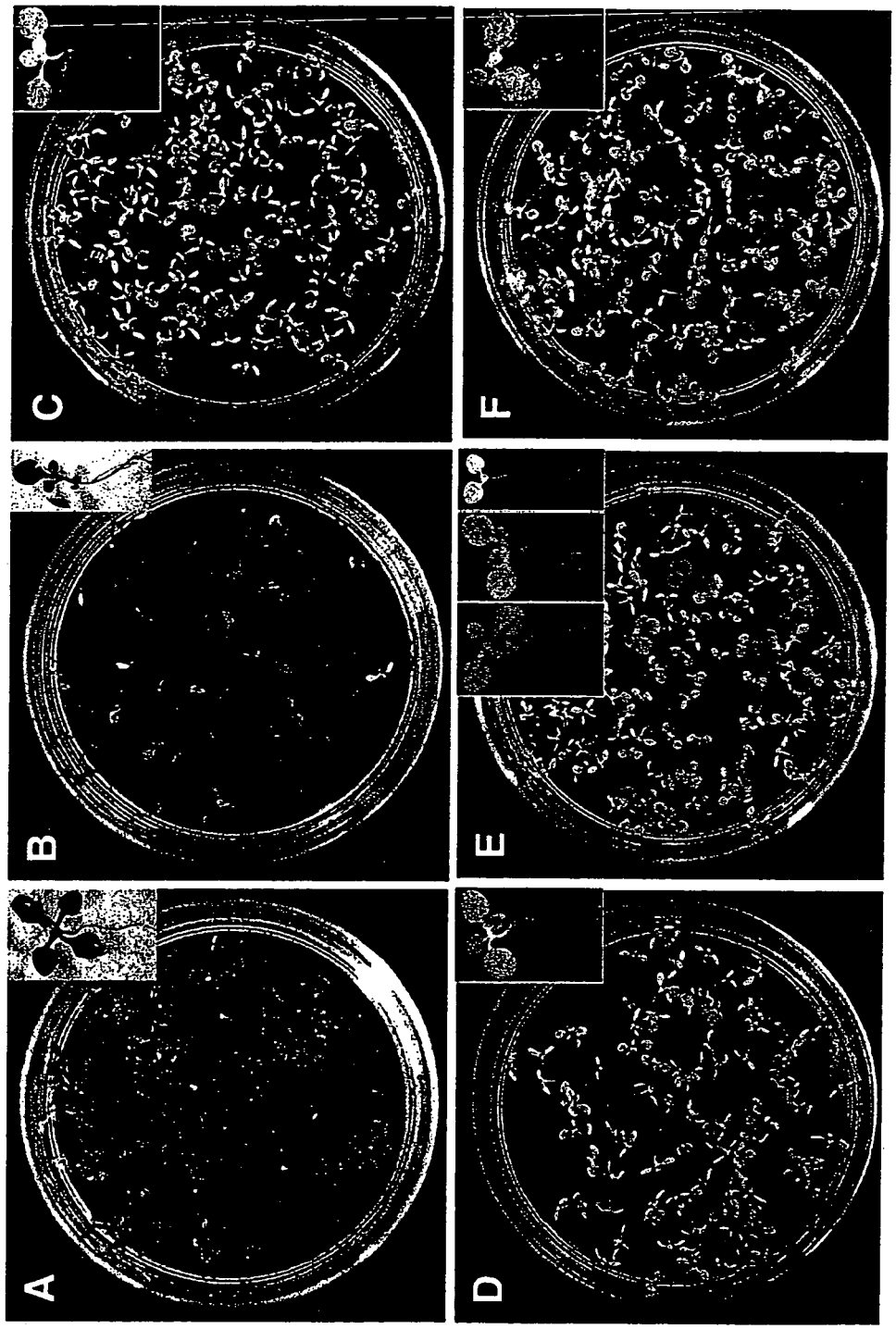
FIG. 2 is a set of photographs showing the expression of the reporter gene GUS in 2-week old transgenic *Arabidopsis* seedlings harboring (A) pGL429, (B) pGL450, (C) pGL419, (D) pGL469, (E) pGL443, or (F) pGL446. The inserts are close-ups of respective transgenic seedlings after staining with the GUS substrate X-gluc. Note the 3 inserts showing different staining patterns in Panel E (about 68% of the plants in Panel E were not stained).

An alternate way to demonstrate the position effect is as follows. We made a construct called pGL443 (construct 5 in FIG. 1) where we used the 35S minimum promoter-GUS gene. The 35S minimum promoter itself has no transcription activity. When this construct is randomly inserted into a plant genome, some neighboring gene promoters/enhancers in certain transgenic plants may activate the GUS expression depending on the activities of the neighboring gene promoters. As shown in FIG. 2, 32% of transgenic *Arabidopsis* seedlings (2 weeks old) containing pGL443 showed the GUS expression exhibiting the position effect. Note that no GUS expression would have been observed if there were no position effect, because the minimum promoter itself has no transcription activity. However, when two copies of the insulator sequence are added at the 5' end of the minimum promoter-GUS gene (pGL446), the transgenic plants did not show GUS expression, demonstrating that the insulator sequence can serve as a buffer to eliminate or reduce the position effect.

Transformed Cells. The invention further relates to a transformed cell or microorganism containing cDNA or a vector which codes for the polypeptide or a fragment or variant thereof and which is capable of expressing the polypeptide. In one embodiment, the transformed cell is a seed cell.

Plant Cell Expression Systems. Transgenic plants may be produced using the DNA constructs of the invention by the DNA-mediated transformation of plant cell protoplasts and subsequent regeneration of the plant from the transformed protoplasts in accordance with procedures well known in the art. Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques.

In plants, transformation vectors capable of introducing polynucleotides containing the insulator sequence are easily designed, and generally contain one or more DNA coding sequences of interest under the transcriptional control of 5' and 3' regulatory sequences. Such vectors generally comprise, operatively linked in sequence in the 5' to 3' direction, an insulator sequence and a promoter sequence that directs the transcription of a downstream heterologous structural DNA in a plant; optionally a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation are described (Schardl et al., *Gene* 61, 1-14, (1987); *Plant Mol Biol.*, 25:989-994 (1994)). Particularly useful vectors for this invention include, but are not limited to pPZP family.

Plant Transformation and Regeneration. A variety of different methods can be employed to introduce such vectors into plant trichome, protoplasts, cells, callus tissue, leaf discs, meristems, etc., to generate transgenic plants, including *Agrobacterium*-mediated transformation, particle gun delivery, microinjection, electroporation, polyethylene glycol-mediated protoplast transformation, liposome-mediated transformation, etc. In general, transgenic plants comprising cells containing and expressing polynucleotides encoding various enzymes can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

The polynucleotides can be introduced either in a single transformation event (all necessary polynucleotides present on the same vector), a co-transformation event (all necessary polynucleotides present on separate vectors that are introduced into plants or plant cells simultaneously), or by independent transformation events (all necessary polynucleotides present on separate vectors that are introduced into plants or plant cells independently). Traditional breeding methods can subsequently be used to incorporate the entire pathway into a single plant. Specific methods for transforming a wide variety of dicots and obtaining transgenic plants are well documented in the literature.

Successful transformation and plant regeneration of transgenic plants have been achieved in the monocots as follows: asparagus (*Asparagus officinalis*; Bytebier et al, *Proc. Natl. Acad. Sci. USA,* 84:5345 (1987)); barley (*Hordeum vulgarae*; Wan & Lemaux, *Plant Physiol.*, 104:37 (1994)); maize (*Zea mays*; Rhodes et al, *Science*, 240:204 (1988); Gordon-Kamm et al, *Plant Cell*, 2:603 (1990); Fromm et al, *Bio/Technology,* 8:833 (1990); Koziel et al, *Bio/Technology*, 11:194 (1993)); oats (*Avena saliva*; Somers et al, *Bio/Technology*, 10:1589 (1992)); orchard grass (*Dactylic glomerata*; Horn et al, *Plant Cell Rep.,* 7:469 (1988)); rice (*Oryza saliva*, including *indica* and *japonica* varieties; Toriyama et al, *Bio/Technology*, 6:10 (1988); Zhang et al, *Plant Cell Rep.,* 7:379 (1988); Luo & Wu, *Plant Mol. Biol. Rep.,* 6:165 (1988); Zhang & Wu, *Theor. Appl. Genet.,* 76:835 (1988); Christou et al, *Bio/Technology,* 9:957 (1991)); rye (*Secale cereale*; De la Pena et al, *Nature,* 325:274 (1987)); sorghum (*Sorghum bicolor*; Cassas et al, *Proc. Natl. Acad. Sci. USA;* 90:11212 (1993)); sugar cane (*Saccharuin* spp.; Bower & Birch, *Plant J.,* 2:409 (1992)); tall fescue (*Festuca arundinacea*; Wang et al, *Bio/Technology,* 10:691 (1992)); turfgrass (*Agrostis palustris*; Zhong et al, *Plant Cell Rep.,* 13:1 (1993)); and wheat (*Triticum aestinum*; Vasil et al, *Bio/Technology,* 10:667 (1992); Weeks et al, *Plant Physiol.,* 102:1077 (1993); Becker et al, *Plant J.,* 5:299 (1994)).

Relevant Plants. The methods of the invention can be carried out with cells from a variety of different plants. As used herein, the term "plant" or "plants" means vascular plants, including both monocots and dicots, and both angiosperms and gymnosperms. Particularly useful plants for exploiting the genetic insulator sequences of the invention include plant and ferns of the genus *Populus, Ermophilia, Lycopersicon, Nicotiana, Cannabis, Pharbitis, Apteria, Psychotria, Mercurialis, Chrysanthemum, Polypodium, Pelargonium, Polytrichiales, Mimulus, Chamomile, Monarda, Solanum, Achillea, Valeriana, Ocimum, Medicago, Aesculus, Newcastelia, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogogstemon, Majorana, Cleome, Cnicus, Parthenium, Ricinocarpos, Parthenium, Hymenaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia,* and *Viscaria.* Plants which may be employed in practicing the present invention include (but are not limited to) tobacco (*Nicotiana tabacum*), potato (*Solanum tuberosum*), soybean (*Glycine max*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*, also known as maize), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (*Pisum* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum. Gymnosperms which may be employed to carrying out the present invention include conifers, including pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Production of Transgenic Plants Comprising a Gene or Multiple Genes of Interest. Plant transformation vectors capable of delivering polynucleotides (genomic DNAs, plasmid DNAs, cDNAs, or synthetic DNAs) can be easily designed. Various strategies can be employed to introduce these DNAs to produce transgenic plants capable of biosynthesizing high levels of a gene product of interest including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.
2. Sequentially transforming plants with plasmids containing each of the encoding DNAs of interest, respectively.
3. Simultaneously cotransforming plants with plasmids containing each of the encoding DNAs, respectively.
4. Transforming plants with a single plasmid containing two or more encoding DNAs of interest.
5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (see, published PCT patent application WO 93/02187).

The use of vectors containing different selectable marker genes to facilitate selection of plants containing two or more different-encoding DNAs is advantageous. Examples of useful selectable marker genes include those conferring resistance to kanamycin, hygromycin, sulphonamides, glyphosate, bialaphos, and phosphinothricin.

Stability for Transgene Expression. As several overexpressed enzymes may be required to produce optimal levels, the phenomenon of co-suppression may influence transgene expression in transformed plants. Several strategies can be employed to avoid this potential problem.

One commonly employed approach is to select and/or screen for transgenic plants that contain a single intact copy of the transgene or other encoding DNA. *Agrobacterium*-mediated transformation technologies are preferred in this regard.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers in addition to the trichome-specific regulatory sequence, for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs. Site-specific recombination in which the endogenous copy of a gene is replaced by the same gene, but with altered expression characteristics, should obviate this problem.

Any of the foregoing methods, alone or in combination, can be employed in order to insure the stability of transgene expression in transgenic plants of the invention.

Kits. Also contemplated by the invention is a kit or kits containing insulator constructs in which the insulator elements of the invention are provided in a DNA receivable vector or plasmid that contains or can be readily adapted by the user to contain the appropriate DNA elements for proper expression of a gene or genes of interest. The insulator element-containing plasmids or vectors of the kit may contain insulator elements, enhancers, a transcription unit, and the gene or genes of interest may be inserted between the insulators, as desired. Alternatively, the constructs of the kit may contain some or all of the necessary genetic elements for proper gene expression, or combinations of these, and the remaining genetic elements may be provided and readily inserted by the user, preferably between the insulator elements in the construct. The insulator element-containing plasmids or vectors may be provided in containers (e.g. sealable test tubes and the like) in the kit and are provided in the appropriate storage buffer or medium for use and for stable, long-term storage. The medium may contain stablizers and may require dilution by the user. Further, the constructs may be provided in a freeze-dried form and may require reconstitution in the appropriate buffer or medium prior to use.

The details of one or more embodiments of the invention are set forth in the accompanying description above. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

Materials and Methods

Constructs. Standard DNA manipulation (restriction digestion, plasmid isolation, cloning, etc.) was performed as described by Sambrook J et al., *Molecular Cloning: A Laboratory Manual*, Second edition (Cold Spring Harbor Laboratory Press, Cold Spring Harbor, N.Y., 1989).

pGL419: Similar to pGL450, the fragment containing two repeats of the perfect palindromic insulator sequence and the CaMV 35S minimum promoter (−51 region) with the TMV RNA Ω leader sequence was PCR-amplified using pSH9 (Holtorf S et al., *Plant Mol Biol* 29, 637-646 (1995)) as the template with the following two primers: 5' GAAGATCTA <u>GAATATATATATATTCGATA</u> <u>GAATATATATATATTCG</u>CAAGACCCTT CC3' (SEQ ID NO:1) (underlined are the insulator sequences) and 5'GGAATTCCATGGATCCCGGGTGTAATTG-TAAATAG3' (SEQ ID NO:2). This fragment was then fused with the GUS-MAS terminator to form pGL416, which was subsequently cloned into pPZP211 (Hajdukiewicz P et al., *Plant Mol Biol* 25, 989-994 (1994)) at the BamHI and XbaI sites, resulting in pGL419.

pGL429: The CaMV 35S minimum promoter (−51 region) with the TMV RNA Ω leader sequence was PCR-amplified using pSH9 (Holtorf S et al., *Plant Mol Biol* 29, 637-646 (1995)) as the template with two primers (5'GAAGATCT-GATATCAAGCTTCGCAAGACCC3' (SEQ ID NO:3) and 5'GGAATTCCATGGATCCCGGGTGTAATTG-TAAATAG3' (SEQ ID NO:2)). The Ω leader sequence can enhance gene expression at the posttranscriptional level (Gallie D R et al., *Nucleic Acids Res* 15, 3257-3273 (1987)). The PCR product, upon cut with BglII and EcoRI, was cloned into pLITMUS28 (New England Biolab, MA, USA) to form pGL400. A GUS-MAS terminator from pSG506 (Gan S, Ph.D. Thesis; *Molecular characterization and genetic manipulation of plant senescence* (University of Wisconsin-Madison, Madison, 1995)) was then cloned into pGL400 at the NcoI and XbaI sites to form the 35S minimum promoter-GUS-MAS terminator (pGL407), which was subsequently cloned into the binary vector pPZP211 at the BamHI and XbaI sites to form pGL429. The 35S-NPTII was part of the pPZP211 sequence (Hajdukiewicz P et al., *Plant Mol Biol* 25, 989-994 (1994)).

pGL443: A fragment containing the CaMV 35S minimum promoter (−51 region; with the TMV RNA Ω leader sequence)-GUS-MAS terminator was cloned into pPZP211 (Hajdukiewicz P et al., *Plant Mol Biol* 25, 989-994 (1994)) at the XbaI site, resulting in pGL443 (and pGL429a in which the fragment was inserted in an opposite orientation compared with that in pGL443).

pGL446: The fragment containing two copies of insulator-35 minimum promoter-GUS-MAS terminator was released from pGL416 (cf. pGL419 construct) by using SpeI and XbaI, and was subsequently cloned into pPZP211 at the XbaI site, forming two constructs, one was named pGL446.

pGL450: The fragment containing two repeats of the perfect palindromic lac Operator (lacO) sequence (Brown M et al., *Cell* 49, 603-612 (1987)) and the CaMV 35S minimum promoter (−51 region) with the TMV RNA Ω leader sequence was PCR-amplified using pSH9 (Holtorf S et al., *Plant Mol Biol* 29, 637-646 (1995)) as the template with the following two primers: 'GAAGATCT<u>ATTGTGAGCGCTCACAATGATA ATTGTGAGCGCTCACAATTCGCAAG</u> ACCCTTCC3' (SEQ ID NO:4) (underlined are the lacO sequences) and 5'GGAATTCCATGGATCCCGGGTGTAATTG-TAAATAG3' (SEQ ID NO:2). This fragment was then cloned into pGL429a at the BamHI site, resulting in pGL450.

pGL469: Like pGL419, the fragment containing one copy of the perfect palindromic insulator sequence and the CaMV 35S minimum promoter (−51 region) with the TMV RNA Ω leader sequence was PCR-amplified using pSH9 as the template with the following two primers: 5'GAAGATCTA<u>GAATATATATATATTC</u>ACTAGTTCGCAAGACCCTTCC3' (SEQ ID NO:5) (underlined is the insulator sequence) and 5'GGAATTCCATGGATCCCGGGTGTAATTG-TAAATAG3' (SEQ ID NO:2)). This fragment was subsequently cloned into pGL429a at the BamHI site to form pGL469.

*Agrobacterium* transformation. The above constructs were transferred into *Agrobacterium tumefaciens* strain ABI using the freeze-thaw method of An G, In *Methods in Enzymology: Recombinant DNA*, Wu R & Grossman L, eds., 292-305 (San Diego, Academic Press, 1987). Briefly, about 2-5 µg of each of the DNA constructs was added to a 1.5-mL microcentrifuge tube containing 100 µL of competent ABI cells, mixed, and the mixture frozen in dry ice-ethanol bath, then placed in 37° C. water bath for 5 minutes. 100 µL of YEP media was added into the tube, and the whole cells in the tube were plated on YEP plate containing 100 mg/L spectinomycin (YEP: 10 g/L Bacto-peptone, 10 g/L Bacto-yeast extracts, 5 g NaCl; for plates, add 10 g/L phytoagar).

Plant transformation and cultivation. The *Agrobacterium* ABI cells containing the various constructs were used to transform *Arabidopsis* (ecotype Columbia) via vacuum infiltration as described by Bechtold N et al., *C R Acad Sci Paris* 316, 1194-1199 (1993). Briefly, about 200 mL YEP medium with 100 µg/L spectinomycin was inoculated with a 10 mL preculture of *Agrobacterium* harboring the respective construct. The cells of overnight culture (28° C., 250 RPM shaker) with ~1.4 $OD_{600}$ was pelleted by centrifugation and resuspended in 200 mL of infiltration medium (½× Murashige-Skoog salts, 1×B5 vitamins, 5% sucrose, 0.5 g MES, 0.044 µM benzylaminopurine and 0.02% Silwet L-77, pH 5.7). The resuspension was transferred into a 250-mL beaker, and a pot of *Arabidopsis* plants that had several flowers was invertedly submerged in the cell suspension and vacuumed for 10-15 min using an air vacuum pump. The plants were allowed to complete their life cycle and the seeds were harvested. After surface-sterilized with 70% ethanol containing 0.1-0.2% Triton X-100, the seeds were sown on MS plates containing kanamycin (50 mg/L) and incubated 23° C. in an *Arabidopsis* growth chamber with 65% relative humidity under ~150 µmol $m^{-2}s^{-1}$ continuous light from a mixture of cool white fluorescent (60%) and incandescent (40%) bulbs. The transgenic seedlings were either assayed for GUS expression or transplanted into soil. The plants were grown in a plant growth facility under similar conditions.

GUS enzyme assays. The GUS assays in transgenic plants were performed histochemically and quantitatively according to the standard protocol of Jefferson R A, Assaying chimeric genes in plants: the GUS gene fusion system, *Plant Mol Biol Rep* 5, 387-405 (1987). X-glucuronide (X-Gluc) was used as substrate for histochemical staining, and 4-methylumbelliferyl-β-D-glucuronide for quantitative assays.

Nuclear protein extraction. Arabidopsis nuclear proteins were isolated in a cold room using a protocol modified from Slomiany B A, *BioTechniques* 28, 938-942 (2000). Briefly, 1-2 g of 2-week old *Arabidopsis* seedlings were ground into powder in liquid nitrogen and homogenized in 6 mL of extraction buffer (10 mM HEPES (pH 7.9), 10 mM KCl, 750 µM spermidine, 150 µM spermine, 0.1 mM EDTA, 0.1 mM EGTA, 1 mM DTT, 20 µM PMSF, 50 µg/mL antipain, 0.5 µg/mL leupeptin, 1 µg/mL pepstatin, 50 µg/mL chymostatin, 1 µg/mL aprotinin). After filtering through 44 µm nylon mesh, each 1 mL of filtrate was mixed with 1 µL NP-40 and kept on ice for 10 minutes. Nuclei was pelleted (12,000×g, 3 min) and resuspended in 4× volume of nuclear storage buffer (50% glycerol, 20 mM HEPES (pH7.9), 60 mM KCl, 0.5 mM EDTA). An equal volume of 0.8 M ammonium sulfate was then added to the suspension. After left on ice for 20 min, the suspension was centrifuged (16,000×g, 5 min), and the supernatant was infiltrated through a G25 column (fine or medium) that had been equilibrated with the column buffer (20% glycerol, 20 mM HEPES (pH7.9), 60 mM KCl, 0.5 mM EDTA) and aliquoted and stored in a −80° C. freezer.

Electrophoretic mobility shift assay (EMSA). DNA probes were labeled with $^{32}P$ by using either Klenow enzyme fill-in or T4 Polynucleotide kinase (Promega, Madison, Wis.) method. About 6,000-7,000 CPM labeled DNA probes were incubated with or without 9 µg (unless otherwise indicated) of nuclear proteins in a buffer (25 mM TrisCi (pH7.75), 10% glycerol, 0.2 µg BSA/µL, 0.1 mM EDTA, 0.05% NP-40, 1 mM DTT, 150 mM NaCl, and 0.2 µg Poly (dI:dC)/µL) on ice for 40 min. The binding reactions were run on 4% acrylamide gel. The gels were analyzed using autoradiography and a phosphoimage analyzer (Fuji Model 2000).

DNA probes. The following oligonucleotides were synthesized and used in electrophoretic mobility shift assays (EMSA). The capital letters indicate the palindromic sequences while the underlined are mutated nucleotides. Naturally mutated form NIm exists in the *Arabidopsis* genome. The small letters are natural sequences flanking the 16-bp palindromic insulator sequence in *Arabidopsis*. The nucleotides in italics are sequences filled by using the Klenow fill-in method.

TABLE 1

DNA probes used

| Probe# | Name | Sequence | | |
|---|---|---|---|---|
| 1 | L18 (Lac operator, 18 bp) | 5'ATTGTGAGCGCTCACAAT3'<br>3'TAACACTCGCGAGTGTTA5' | (SEQ ID NO:6)<br>(SEQ ID NO:38) | |
| 2 | L31 (Lac operator, 31 bp) | 5'cttctaATTGTGAGCGCTCACAATgaaaaag3'<br>3'gaagatTAACACTCGCGAGTGTTActttttc5' | (SEQ ID NO:7)<br>(SEQ ID NO:8) | |
| 3 | NI16 (Native insulator, 16 bp) | 5'GAATATATATATATTC3'<br>3'CTTATATATATATAAG5' | (SEQ ID NO:9)<br>(SEQ ID NO:10) | |
| 4 | NI29 (Native insulator, 29 bp) | 5'cttctaGAATATATATATATTCgaaaaag3'<br>3'gaagatCTTATATATATATAAGctttttc5' | (SEQ ID NO:11)<br>(SEQ ID NO:12) | |
| 5 | NIm (Naturally mutated insulator, 29 bp) | 5'cttctaGAATATAT<u>G</u>TATATTCgaaaaag3'<br>3'gaagatCTTATATA<u>C</u>ATATAAGctttttc5' | (SEQ ID NO:13)<br>(SEQ ID NO:14) | |
| 6 | M1 (Mutated insulator, 29 bp) | 5'cttcta<u>ACC</u>TATATATATATTCgaaaaag3'<br>3'gaagat<u>TGG</u>ATATATATATAAGctttttc5' | (SEQ ID NO:15)<br>(SEQ ID NO:16) | |
| 7 | M2 (Mutated insulator, 29 bp) | 5'cttctaGAA<u>GC</u>GATATATATTCgaaaaag3'<br>3'gaagatCTT<u>CG</u>CTATATATAAGctttttc5' | (SEQ ID NO:17)<br>(SEQ ID NO:18) | |
| 8 | M3 (Mutated insulator, 29 bp) | 5'cttctaGAATAT<u>CGC</u>GATATTCgaaaaag3'<br>3'gaagatCTTATA<u>GCG</u>CTATAAGctttttc5' | (SEQ ID NO:19)<br>(SEQ ID NO:20) | |
| 9 | M4 (Mutated insulator, 29 bp) | 5'cttctaGAATAT<u>C</u>TATATATTCgaaaaag3'<br>3'gaagatCTTATA<u>G</u>ATATATAAGctttttc5' | (SEQ ID NO:21)<br>(SEQ ID NO:22) | |
| 10 | M5 (Mutated insulator, 29 bp) | 5'cttctaGAATATA<u>G</u>ATATATTCgaaaaag3'<br>3'gaagatCTTATAT<u>C</u>TATATAAGctttttc5' | (SEQ ID NO:23)<br>(SEQ ID NO:24) | |
| 11 | M6 (Mutated insulator, 29 bp) | 5'cttctaGAATATAT<u>C</u>TATATTCgaaaaag3'<br>3'gaagatCTTATATA<u>G</u>ATATAAGctttttc5' | (SEQ ID NO:25)<br>(SEQ ID NO:26) | |
| 12 | M7 (Mutated insulator, 29 bp) | 5'cttctaGAATATATA<u>G</u>ATATTCgaaaaag3'<br>3'gaagatCTTATATAT<u>C</u>TATAAGctttttc5' | (SEQ ID NO:27)<br>(SEQ ID NO:28) | |

The palindromic sequence portion of the insulator sequence in TABLE 1 are as follows:

| | | |
|---|---|---|
| NI | 5'GAATATATATATATTC3', | (SEQ ID NO:9) |
| NIm | 5'GAATATAT<u>G</u>TATATTC3', | (SEQ ID NO:29) |
| M1: | 5'<u>ACC</u>TATATATATATTC3', | (SEQ ID NO:30) |
| M2 | 5'GAA<u>GC</u>GATATATATTC3', | (SEQ ID NO:31) |
| M3 | 5'GAATAT<u>CGC</u>GATATTC3', | (SEQ ID NO:32) |
| M4 | 5'GAATAT<u>C</u>TATATATTC3', | (SEQ ID NO:33) |
| M5 | 5'GAATATA<u>G</u>ATATATTC3', | (SEQ ID NO:34) |
| M6 | 5'GAATATAT<u>C</u>TATATTC3', | (SEQ ID NO:35) |
| and | | |
| M7 | 5'GAATATATA<u>G</u>ATATTC3', | (SEQ ID NO:36) |

EXAMPLE 2

Two Copies of the 16-bp Palindromic Sequence have Genetic Insulator Activity that Blocks the 35S cis Elements from Directing the Expression of the $P_{35Smini}$-GUS An eukaryotic promoter can be bidirectionalized by fusing a minimum promoter-gene construct at its 5' end in opposite orientation. One example is pGL429, where the CaMV 35 minimum promoter-GUS-MAS terminator chimeric gene (hereafter $P_{35Smini}$-GUS) is fused, in opposite orientation, with the 35S promoter directing the NPTII (kanamycin resistant) gene (construct 1 in FIG. 1). In addition, we generated 78 transgenic Arabidopsis plants harboring this pGL429 construct and found that all of them displayed constitutive expression of the reporter gene GUS. (TABLE 2 and FIG. 2A). This suggests that the cis elements of the 35S promoter exert their effect on the neighboring $P_{35Smini}$-GUS construct.

However, when two copies of a 16-bp palindromic sequence 5'GAATATATATATATTC3' (SEQ ID NO:9) were inserted between the 35S promoter and the $P_{35Smini}$-GUS as shown in pGL419 (construct 3 in FIG. 1), the effect of the cis elements of the 35S promoter on the $P_{35Smini}$-GUS was completely blocked because none of the 133 independent pGL419 transgenic Arabidopsis plants showed the expression of the reporter gene (TABLE 2 and FIG. 2C).

TABLE 2

Expression of the reporter gene GUS in transgenic Arabidopsis lines

| Constructs | Total lines | Lines with GUS staining (%) | Comments |
|---|---|---|---|
| pGL429 | 78 | 78 (100%) | Bidirectional promoter |
| pGL450 | 196 | 196 (100%) | No insulating |

TABLE 2-continued

Expression of the reporter gene GUS
in transgenic *Arabidopsis* lines

| Constructs | Total lines | Lines with GUS staining (%) | Comments |
|---|---|---|---|
| pGL419 | 133 | None (0%) | Insulating |
| pGL469 | 127 | None (0%) | insulating |
| pGL443 | 186 | 60 (32%) | Enhancer trap, no insulating |
| pGL446 | 194 | None (0%) | Insulating |

EXAMPLE 3

Two Copies of the Palindromic lac Operator Sequence Failed to Block the 35S Promoter from Directing the $P_{35Smini}$-GUS Expression The data in EXAMPLE 2 suggest that the 2 copies of the palindromic sequence block the 35S cis elements from directing the $P_{35Smini}$-GUS. However, the blockage could result from (a) the spacer effect of the 2 copies of the palindromic sequence and/or (b) the formation of potential cruciform (cross-shaped) structure of the palindromic sequence. To test these possibilities, we constructed pGL450 in which 2 copies of the modified lac Operator (lacO) sequence were used to replace the 2 copies of the 16-bp insulator sequence. The modified lacO sequence is 18 bp in length (2 bp longer than the insulator). Like the insulator sequence, the modified lacO (5'ATTGTGAGCGCTCACAAT3' (SEQ ID NO:6)) is also a perfect palindromic sequence (Brown M et al., lac repressor can regulate expression from a hybrid SV40 early promoter containing a lac operator in animal cells, *Cell* 49, 603-612 (1987)). We generated 196 independent transgenic *Arabidopsis* lines harboring pGL450 and found that all of the plants, like those plants harboring pGL429 but in contrast to those pGL419 plants, displayed constitutive GUS expression (TABLE 2 and FIG. 2B). This data shows that the blockage of the two copies of the insulator is not due to its spacer effect, and that the palindromic nature of the sequence is not necessary or sufficient for preventing the 35S cis elements from directing the GUS expression.

EXAMPLE 4

One Copy of the 16-bp Palindromic Sequence is Sufficient for Genetic Insulation

We further constructed pGL469 (construct 4 in FIG. 1) in which only one copy of the insulator sequence was used but otherwise the construct is the same as pGL419. All 127 independent transgenic *Arabidopsis* lines generated showed no GUS expression (TABLE 2 and FIG. 2D), indicating that one copy of the insulator is sufficient for playing its insulating role.

EXAMPLE 5

The Insulator Prevents Transgene From Position Effect of Neighboring Genes of Plants A position effect on a transgene is generally exerted by the promoters/enhancers of neighboring genes. This position effect can be demonstrated in either of the following two ways: one is to use a full promoter such as the constitutive 35S promoter fused to the reporter gene GUS, transgenic plants containing this construct should display a spectrum of the GUS expression level, with some plants expressed at a very higher level and some other plants at a much lesser level. The addition of the insulator at the 5' end of the promoter should result in a relatively even level of GUS expression with no or little variation among all transgenic plants. This is a quantitative way to show position effect and the function of an insulator. However, this quantitative method can be complicated by the number of T-DNA insertion in the plant genome and the number of T-DNA repeats in a single insertion site. Because of this complexity, we used an alternative way to demonstrate the position effect: the enhancer trap strategy.

In this enhancer trap strategy, a minimum promoter is fused to a reporter gene such as GUS. This chimeric GUS gene is oriented towards the right border of T-DNA. When the construct inserts in the proximity of a chromosomal gene in plants, the neighboring gene promoter or enhancer of the plant genes may or may not direct the expression of the reporter, depending on the position of the insertion, i.e., in a population of enhancer transgenic lines, some plants will display no expression of the reporter gene while some other transgenic lines may show the reporter gene expression in certain tissues at certain developmental stages. We constructed pGL443 (an enhancer trap construct, see, construct 5 in FIG. 1) and pGL446 to test qualitatively if the insulator can indeed eliminate the reporter gene expression resulting from position effect. pGL446 is identical with pGL443 except that there are 2 copies of the insulator sequence at the 5' end of the enhancer trap construct (construct 5 in FIG.1). About 32% or 60 of the 186 pGL443 transgenic *Arabidopsis* lines showed GUS staining at 2-week old seedling stage (TABLE 2, and FIG. 2E). The GUS staining pattern (as well as intensity) varied, with some lines showing staining in young leaves and roots while some other lines exclusively in roots or meristem (inserts in FIG. 2E). In contrast, there was no single line harboring pGL446 displaying any GUS staining (TABLE 2 and FIG. 2F).

EXAMPLE 6

The Insulator Interacts Specifically With Nuclear Proteins to Form a Complex

As described above, both the 16-bp insulator and the 18-bp lacO are perfect palindromic sequences that may potentially form cruciform secondary structures, and the formation of the secondary structure itself may block the effect of other promoter elements on the reporter gene expression. However, the lacO sequence failed to insulate the reporter gene expression (construct 2, TABLE 2 and FIG. 2B), suggesting that the potential cruciform structure per se is not necessary or sufficient for insulating the effect of neighboring genes, and that the insulating effect appears to be sequence specific.

Figure 3:
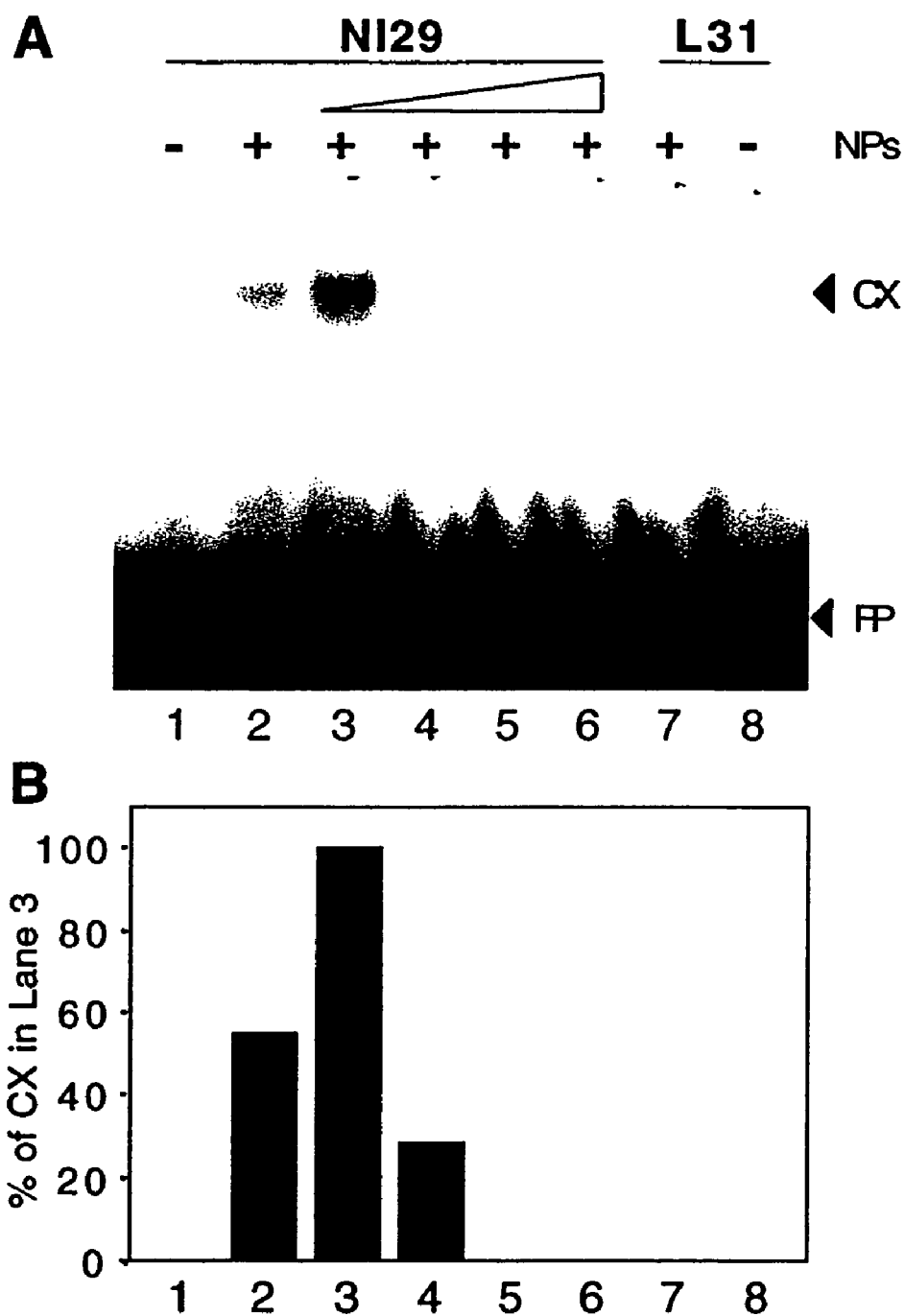
FIG. 3 shows the formation of the insulator-nuclear protein complex (CX) revealed by electrophoretic mobility shift assay (EMSA).

We therefore hypothesized that the insulating role of the insulator is achieved by interacting specifically with plant nuclear proteins. To test this hypothesis, we isolated *Arabidopsis* nuclear proteins and performed electrophoretic mobility shift assays (EMSA). We found that the $^{32}$P-labeled insulator interacted with 5 μg of the *Arabidopsis* nuclear protein extract to form a unique complex band on the acrylamide gels (Lane 2 in FIG. 3). The intensity of the complex was increased with 9 μg of the nuclear protein extract (Lane 3 in FIG. 3). The intensity of the complex was sharply decreased in the presence of 0-, 2-, 20-, or 200-fold molar excess of the cold insulator competitor (Lanes 3 through 6). In contrast, the labeled lacO sequence did not form any complex (Lane 7 in FIG. 3).

EXAMPLE 7

Figure 4:
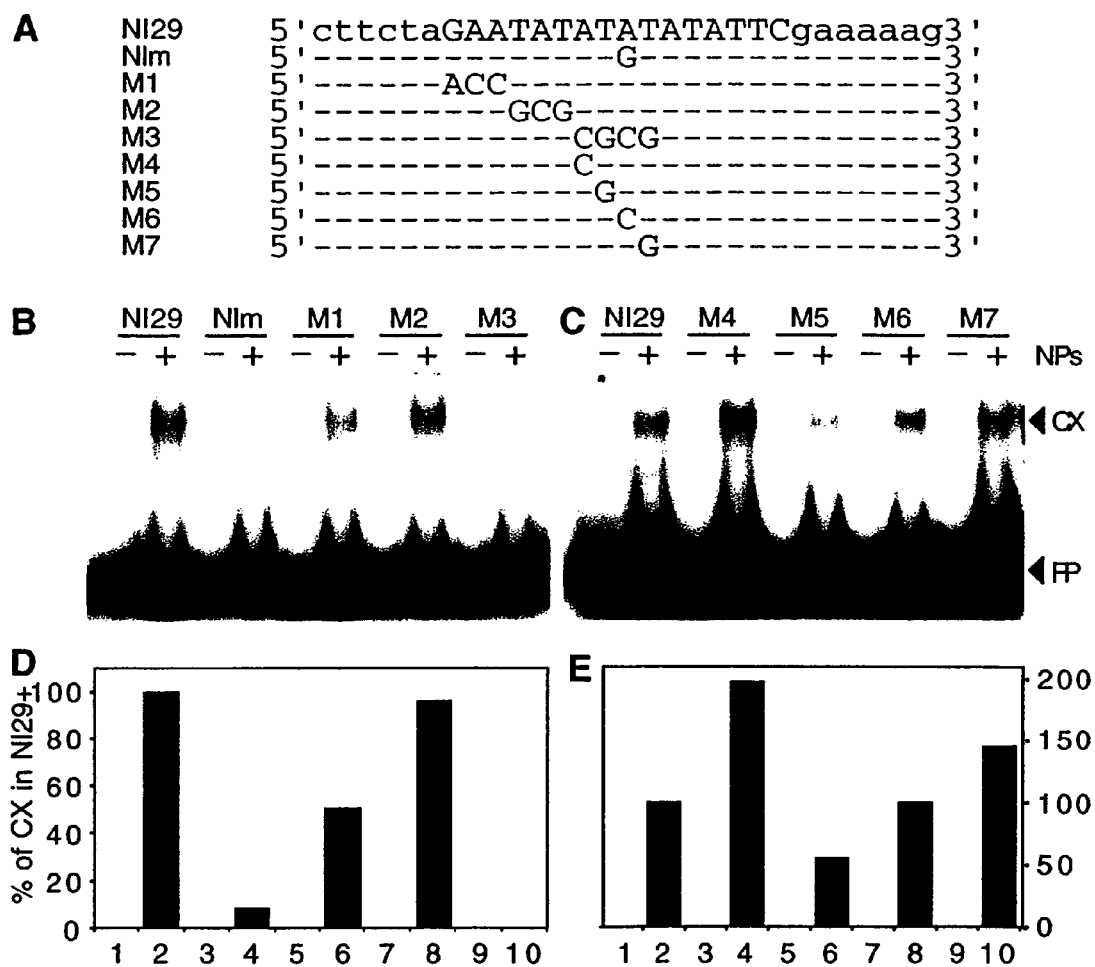
FIG. 4 shows the effects of mutations in the insulator on CX formation.

Naturally Occurring A→G Transition Significantly Reduced the Formation of the Insulator-Nuclear Protein Complex The DNA region containing the insulator sequence in *Arabidopsis* are apparently recently duplicated (Gan S, Ph.D. Thesis; *Molecular characterization and genetic manipulation of plant senescence* (University of Wisconsin-Madison, Madison, 1995)). The sequences of both copies are identical except for 1-bp transition change in the palindrome region. As shown in FIG. 4A, the A→G transition makes the perfect palindrome (we named it native insulator, or NI) a non-perfect one (called NIm for native insulator with a mutation). We were interested in knowing if this naturally occurring NIm sequence could also specifically interact with the nuclear protein extract. The migration of the labeled NIm did shift on the acrylamide gel but the amount of the complex formed was reduced to 8.3% compared with that of non-mutant N129 (Lane 4 vs. Lane 2 in FIGS. 4B and 4D).

EXAMPLE 8

The Effect of Artificial Mutations in the Insulator on the Complex Formation

We used the electrophoretic mobility shift assay (EMSA) to further investigate the function of nucleotides of the insulator in interacting with the nuclear protein extract. We first made three mutated insulators, two of them with mutations in the potential "stem" region of the palindrome (M1 and M2 in FIG. 4A) and the other one in potential "tetranucleotide loop" (M3). All these are transversion mutations. As shown in FIG. 4B and 4D, the ability of M1 interacting with the nuclear extract was reduced to 50.5% of the natural insulator N129 while M2 remained near 95% of its binding activity. However, the transversion mutations in the potential loop region (M3) completely abolished the formation of the complex (Lane 10 in FIGS. 4B and 4D).

As shown in FIG. 4A, the M3 mutant that lost its ability of interacting with the nuclear extract has 4 transversional changes in the potential loop region. To investigate the role of individual nucleotides, we further made 4 mutants, each mutant with only one transversion (M4-M7 in FIG. 4A). Interestingly, except for the M5 that had a reduced nuclear protein-binding activity (55.2%), other three mutants remained (M6) the same as or even outperformed over the native insulator N129. The M7 showed a 45% increase in nuclear protein-binding activity and the activity of the M4 was almost doubled (FIGS. 4C and 4E).

Based upon these results, an initial consensus sequence was obtained.

TABLE 3

Sequence comparison

| Seq. Name | SEQ ID NO | Sequence |
|---|---|---|
| NI | (SEQ ID NO:9) | 5'G A A T A T  A T A T ATATTC3' |
| NIm (Inactive) | (SEQ ID NO:29) | 5'G A A T A T  A T <u>G</u> T ATATTC3' |
| M1: | (SEQ ID NO:30) | 5'<u>A C C</u> T A T  A T A T ATATTC3' |
| M2 | (SEQ ID NO:31) | 5'G A A <u>G C G</u> A T A T ATATTC3' |
| M3 (Inactive) | (SEQ ID NO:32) | 5'G A A T A T <u>C G C G</u> ATATTC3' |
| M4 | (SEQ ID NO:33) | 5'G A A T A T <u>C</u> T A T ATATTC3' |
| M5 | (SEQ ID NO:34) | 5'G A A T A T A <u>G</u> A T ATATTC3' |
| M6 | (SEQ ID NO:35) | 5'G A A T A T A T <u>C</u> T ATATTC3' |
| M7 | (SEQ ID NO:36) | 5'G A A T A T A T A <u>G</u> ATATTC3' |
| Initial Consensus | (SEQ ID NO:37) | 5'$N_1$ $N_1$ $N_1$ $N_1$ $N_1$ $N_1$ $N_2$ $N_2$ $N_3$ $N_2$ ATATTC3' |

$N_1$ is any nucleotide
$N_2$ is not G; and
$N_2N_2N_3N_2$ is not CGCG

The foregoing description has been presented only for the purposes of illustration and is not intended to limit the invention to the precise form disclosed, but by the claims appended hereto.

What is claimed is:

1. A method for insulating the expression of a transgenic polypeptide from cis acting regulatory elements in the plant chromosome into which a polynucleotide coding for the expressed transgenic polypeptide has integrated, comprising:
    transfecting a plant cell with a polynucleotide construct comprising
    (a) a genetic insulator, comprising at least one copy of a polynucleotide having the sequence set forth in SEQ ID NO:9;
    (b) a transcription initiation region; and
    (c) a structural polynucleotide encoding the transgenic polypeptide;
    wherein the expression of the transgenic polypeptide from the integrated polynucleotide is insulated from cis acting regulatory elements in the plant chromosome into which the polynucleotide coding for the expressed polypeptide has integrated, and
    wherein, the transcription initiation region is heterologous to the genetic insulator comprising SEQ ID: 9.

2. The method according to claim 1 wherein the genetic insulator, the transcription initiation region and the structural polynucleotide are operatively associated.

3. The method according to claim 1 wherein the transfected polynucleotide construct integrates into a chromosome of the plant cell.

4. A method for insulating the expression of a transgenic polypeptide from cis acting regulatory elements in the plant chromosome into which a polynucleotide coding for the expressed transgenic polypeptide has integrated, comprising:
    transfecting a plant cell with a polynucleotide construct comprising
    (a) a genetic insulator, comprising more than one copy of a polynucleotide having the sequence set forth in SEQ ID NO:9;
    (b) a transcription initiation region; and
    (c) a structural polynucleotide encoding the transgenic polypeptide;
    wherein the expression of the transgenic polypeptide from the integrated polynucleotide is insulated from cis acting regulatory elements in the plant chromosome into which the polynucleotide coding for the expressed polypeptide has integrated, and
    wherein, the transcription initiation region is heterologous to the genetic insulator comprising SEQ ID: 9.

* * * * *